United States Patent
Tabacchi et al.

(10) Patent No.: US 6,673,861 B2
(45) Date of Patent: Jan. 6, 2004

(54) INVERSE LATICES SELF-INVERTIBLE WITH RESPECT TO WHITE MINERAL OILS, SQUALANE, HYDROGENATED POLYISOBUTENE, ISOHEXADECANE OR ISODODECANE AND COSMETIC, DEMOCOSMETIC, DERMOPHARMACEUTICAL OR PHARMACEUTICAL COMPOSITIONS COMPRISING THEM

(75) Inventors: Guy Tabacchi, Castres (FR); Jean-Pierre Boiteux, Saix (FR); Chantal Almaric, Blan (FR); Nelly Michel, Maisons Alfort (FR); Paul Mallo, Chatou (FR)

(73) Assignee: Societe d'Exploitation de Produits pour les Industries Chimiques Seppic, Paris Cedex (FR)

( * ) Notice: Subject to any disclaimer, the term of this patent is extended or adjusted under 35 U.S.C. 154(b) by 269 days.

(21) Appl. No.: 09/849,313

(22) Filed: May 7, 2001

(65) Prior Publication Data

US 2001/0051686 A1 Dec. 13, 2001

(30) Foreign Application Priority Data

May 5, 2000 (FR) .............................................. 00 05790

(51) Int. Cl.$^7$ .................................................. C08F 2/16
(52) U.S. Cl. ........................ 524/458; 523/201; 526/87; 526/201; 526/207; 526/211; 526/213
(58) Field of Search .......................... 523/201; 524/458; 526/87, 91, 93; 525/902

(56) References Cited

U.S. PATENT DOCUMENTS 5,185,395 A    2/1993  Robinson et al.

FOREIGN PATENT DOCUMENTS

| EP | 1 010 708 | 6/2000 |
| FR | 2 721 511 | 12/1995 |
| FR | 2 774 688 | 8/1999 |
| FR | 2 774 996 | 8/1999 |
| FR | 2 782 086 | 2/2000 |
| FR | 2 785 801 | 5/2000 |
| WO | WO 00/32639 | 6/2000 |

*Primary Examiner*—Helen L. Pezzuto
(74) *Attorney, Agent, or Firm*—Young & Thompson

(57) ABSTRACT

Composition comprising an oil phase, an aqueous phase, at least one emulsifying agent of water-in-oil (W/O) type and at least one emulsifying agent of oil-in-water (O/W) type in the form of a self-invertible inverse latex comprising from 20% to 70% by weight, and preferably from 25% to 50% by weight of a branched or crosslinked polyelectrolyte, characterized in that the said polyelectrolyte is either a homopolymer based on a monomer having a partially or completely salified strong acid functional group or a copolymer based on at least one monomer having a partially or completely salified strong acid functional group copolymerized with acrylamide and characterized in that the constituent solvent of the oil phase is chosen from white mineral oils, squalane, hydrogenated polyisobutene, isohexadecane or isododecane. Cosmetic, dermocosmetic, dermopharmaceutical or pharmaceutical composition comprising them.

24 Claims, No Drawings

INVERSE LATICES SELF-INVERTIBLE WITH RESPECT TO WHITE MINERAL OILS, SQUALANE, HYDROGENATED POLYISOBUTENE, ISOHEXADECANE OR ISODODECANE AND COSMETIC, DEMOCOSMETIC, DERMOPHARMACEUTICAL OR PHARMACEUTICAL COMPOSITIONS COMPRISING THEM

The present application relates to inverse water-in-oil latices, to their process of preparation and to their application as thickeners and/or emulsifiers for skincare and haircare products and for the manufacture of cosmetic, dermocosmetic, dermopharmaceutical or pharmaceutical preparations.

Synthetic thickening polymers, provided in the form of inverse latices, are disclosed as being able to be used in the manufacture of topical compositions in the French patent applications published under the numbers 2 721 511, 2 733 805, 2 774 688, 2 774 996 and 2 782 086 and in the European patent application published under the number EP 0 503 853.

However, some of them sometimes produce intolerance reactions with some types of sensitive skin.

That is why the Applicant Company has taken an interest in looking for novel polymer emulsions which are better tolerated by the skin than those of the state of the art.

A subject-matter of the invention is a composition comprising an oil phase, an aqueous phase, at least one emulsifying agent of water-in-oil (W/O) type and at least one emulsifying agent of oil-in-water (O/W) type in the form of a self-invertible inverse latex comprising from 20% to 70% by weight and preferably from 25% to 50% by weight of a branched or crosslinked polyelectrolyte, characterized in that the said polyelectrolyte is either a homopolymer based on a monomer having a partially or completely salified strong acid functional group or a copolymer based on at least one monomer having a partially or completely salified strong acid functional group copolymerized with acrylamide and characterized in that the constituent solvent of the oil phase is chosen from white mineral oils, squalane, hydrogenated polyisobutene, isohexadecane or isododecane.

Isohexadecane, which is identified in Chemical Abstracts by the number RN=93685-80-4, is a mixture of $C_{12}$, $C_{16}$ and $C_{20}$ isoparaffins comprising at least 97% of $C_{16}$ isoparaffins, among which the main constituent is 2,2,4,4,6,8,8-heptamethylnonane (RN=4390-04-9). It is sold in France by Bayer.

Isododecane is sold in France by Bayer.

Hydrogenated polyisobutene is sold in France by Ets B. Rossow et Cie under the name Parleam-Polysynlane™. It is mentioned in: Michel and Irene Ash; Thesaurus of Chemical Products, Chemical Publishing Co. Inc., 1986, Volume I, page 211 (ISBN 0 7131 3603 0).

Squalane is sold in France by Sophim under the name Phytosqualan™. It is identified in Chemical Abstracts by the number RN=111-01-3. It is a mixture of hydrocarbons comprising more than 80% by weight of 2,6,10,15,19,23-hexamethyltetracosane.

The term "white mineral oil" is understood to mean, in the context of the present invention, a white mineral oil in accordance with the FDA regulations 21 CFR 172.878 and FR 178.3620(a).

A more particular subject-matter of the invention is a composition as defined above in which the constituent white mineral oil of the oil phase is Marcol™52. Marcol™52 is a commercial oil corresponding to the definition of liquid paraffins of the French Pharmacopoeia.

According to a second specific aspect of the present invention, the constituent solvent of the oil phase of the inverse latex is hydrogenated polyisobutene.

According to a third specific aspect of the present invention, the constituent solvent of the oil phase of the inverse latex is squalane.

According to a fourth specific aspect of the present invention, the constituent solvent of the oil phase of the inverse latex is isohexadecane.

According to a fifth specific aspect of the present invention, the constituent solvent of the oil phase of the inverse latex is isododecane.

The term "branched polymer" denotes a nonlinear polymer which has pendant chains, so as to obtain a high state of entanglement when this polymer is dissolved in water, resulting in very high viscosities at a low gradient.

The term "crosslinked polymer" denotes a non-linear polymer which exists in the state of a three-dimensional network which is insoluble in water but swellable in water and which thus results in the production of a chemical gel.

The composition according to the invention can comprise crosslinked units and/or branched units.

The term "emulsifying agent of the water-in-oil type" denotes emulsifying agents having an HLB value which is sufficiently low to provide water-in-oil emulsions, such as the surface-active polymers sold under the name of Hypermer™ or such as sorbitan esters, for example the sorbitan monooleate sold by Seppic under the tradename of Montane 80™ or the sorbitan isostearate sold by Seppic under the tradename of Montane 70™. These emulsifying agents can also include the sorbitan oleate ethoxylated with 5 mol of ethylene oxide sold by Seppic under the tradename of Montanox™ 81.

The term "emulsifying agent of the oil-in-water type" denotes emulsifying agents having an HLB value which is sufficiently high to provide oil-in-water emulsions, such as ethoxylated sorbitan esters, for example the sorbitan oleate ethoxylated with 20 mol of ethylene oxide sold by Seppic under the name of Montanox™80, the ethoxylated castor oil comprising 40 mol of ethylene oxide sold by Seppic under the name of Simulsol™ OL 50, the ethoxylated sorbitan laurate comprising 20 mol of ethylene oxide sold by Seppic under the name of Moneanox™20 or the ethoxylated lauryl alcohol comprising 7 mol of ethylene oxide sold by Seppic under the name of Simulsol™ P7.

Emulsifying agents having an HLB value which is sufficiently high to provide oil-in-water emulsions also include the compounds of formula (I):

$$R_1-O-[CH(R_2)-CH_2-O]_n-(G)_x-H \qquad (I),$$

in which $R_1$ represents a saturated or unsaturated and linear or branched hydrocarbonaceous radical comprising from 1 to 30 carbon atoms, $R_2$ represents a hydrogen atom or an alkyl radical comprising 1 or 2 carbon atoms, G represents the residue of a saccharide, x represents a decimal number between 1 and 5 and n is equal either to zero or to an integer between 1 and 30.

The term "residue of a saccharide" denotes, for G, a bivalent radical resulting from the removal on a sugar molecule, on the one hand, of a hydrogen atom of a hydroxyl group and, on the other hand, of the anomeric hydroxyl group. The term "saccharide" denotes in particular glucose or dextrose, fructose, mannose, galactose, altrose, idose, arabinose, xylose, ribose, gulose, lyxose, maltose, maltotriose, lactose, cellobiose, dextran, talose, allose, raffinose, laevoglucan, cellulose or starch. The oligomeric structure (G) can exist under any form of isomerism, whether optical isomerism, geometrical isomerism or positional isomerism. It can also represent a mixture of isomers.

In the formula (I) as defined above, the radical:

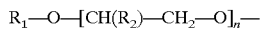

is bonded to G via the anomeric carbon, so as to form an acetal functional group. The divalent group —[CH($R_2$)—$CH_2$—O]$_n$— represents either a chain composed solely of ethoxyl groups ($R_2$=H) or a chain composed solely of propoxyl groups ($R_2$=$CH_3$) or a chain composed both of ethoxyl groups and of propoxyl groups. In the latter case, the fragments —$CH_2$—$CH_2$—O— and —CH($CH_3$)—$CH_2$—O— are distributed in the said chain in a block or random fashion.

The number x, which represents, in the formula (I), the mean degree of polymerization of the saccharide, is more particularly between 1 and 3, in particular between 1.05 and 2.5, very particularly between 1.1 and 2.0 and preferably less than or equal to 1.5.

Emulsifying surface-active agents having an HLB value which is sufficiently high to provide oil-in-water emulsions include more particularly the compounds of formula (I) as defined above in which G represents the glucose residue or the xylose residue and/or in which n is equal to 0 and/or in which $R_1$ represents a radical comprising from 8 to 18 carbon atoms and more particularly in which $R_1$ represents a radical chosen from the octyl, decyl, undecyl, dodecyl, tetradecyl or hexadecyl radicals, the said radicals being linear or branched.

Commercial products comprising the said compounds include, for example:

Simulsol™SL8, sold by Seppic, which is an aqueous solution comprising between approximately 35% and 45% by weight of a mixture of alkyl polyglycosides consisting of between 45% by weight and 55% by weight of a compound of formula (I) in which G represents the glucose residue, x is equal to about 1.45, n is equal to 0 and $R_1$ represents a decyl radical and between 45% by weight and 55% by weight of a compound of formula (I) in which G represents the glucose residue, x is equal to approximately 1.45, n is equal to 0 and $R_1$ represents an octyl radical;

Simulsol™ SL10, sold by Seppic, which is an aqueous solution comprising between approximately 40% by weight and 50% by weight of a mixture of alkyl polyglycosides consisting of approximately 85% by weight of a compound of formula (I) in which G represents the glucose residue, x is equal to approximately 1.45, n is equal to 0 and $R_1$ represents a decyl radical, approximately 7.5% by weight of a compound of formula (I) in which G represents the glucose residue, x is equal to approximately 1.45, n is equal to 0 and $R_1$ represents a dodecyl radical and approximately 7.5% by weight of a compound of formula (I) in which G represents the glucose residue, the number x is equal to approximately 1.45, n is equal to 0 and $R_1$ represents a tetradecyl radical;

Simulsol™ SL11, sold by Seppic, which is an aqueous solution comprising between approximately 40% by weight and 50% by weight of a mixture of alkyl polyglycosides consisting of approximately 85% by weight of formula (I) in which G represents the glucose residue, x is equal to approximately 1.45, n is equal to 0 and $R_1$ represents an undecyl radical; or Simulsol™ SL26, sold by Seppic, which is an aqueous solution comprising between approximately 40% by weight and 55% by weight of a mixture of alkyl polyglycosides consisting of approximately 70% by weight of a compound of formula (I) in which G represents the glucose residue, x is equal to approximately 1.45, n is equal to 0 and $R_1$ represents a dodecyl radical, approximately 25% by weight of a compound of formula (I), in which G represents the glucose residue, x is equal to approximately 1.45, n is equal to 0 and $R_1$ represents a tetradecyl radical and approximately 5% by weight of a compound of formula (I) in which G represents the glucose residue, x is equal to approximately 1.45, n is equal to 0 and $R_1$ represents a hexadecyl radical.

The strong acid functional group of the monomer comprising it is in particular the sulphonic acid functional group or the phosphonic acid functional group, partially or completely salified. The said monomer can be, for example, partially or completely salified styrenesulphonic acid. It is preferably 2-methyl-2-[(1-oxo-2-propenyl)amino]-1-propanesulphonic acid, partially or completely salified in the form of an alkali metal salt, such as, for example, the sodium salt or the potassium salt, of the ammonium salt or of a salt of an aminoalcohol, such as, for example, the monoethanolamine salt.

According to a sixth specific aspect of the present invention, the polyelectrolyte included in the inverse latex as defined above is a copolymer comprising, in molar proportions, from 30% to 50% of 2-methyl-2-[(1-oxo-2-propenyl)amino]-1-propanesulphonic acid (AMPS™), salified in the form of the sodium salt or of the ammonium salt, and from 50% to 70% of acrylamide.

According to a seventh specific aspect of the present invention, the polyelectrolyte included in the inverse latex as defined above is a homopolymer of 2-methyl-2-[(1-oxo-2-propenyl)amino]-1-propanesulphonic acid salified in the form of the sodium salt or of the ammonium salt.

A subject-matter of the invention is, more particularly, a composition as defined above, characterized in that the polyelectrolyte is crosslinked and/or branched with a diethylenic or polyethylenic compound in the molar proportion, expressed with respect to the monomers employed, of 0.005% to 1%, more particularly of 0.01% to 0.5% and very particularly of 0.1% to 0.25%. The crosslinking agent and/or the branching agent is chosen from diallyloxyacetic acid or one of its salts, such as sodium diallyloxyacetate, ethylene glycol dimethacrylate, ethylene glycol diacrylate, diallylurea, trimethylolpropane triacrylate, methylenebis (acrylamide), triallylamine or a mixture of these compounds.

According to an eighth specific aspect of the present invention, the polyelectrolyte included in the inverse latex as defined above is crosslinked with triallylamine.

The inverse latex as defined above generally comprises from 4% to 10% by weight of emulsifying agents. Generally, from 20% to 50% and more particularly from 25% to 40% of the total weight of the emulsifiers are of the water-in-oil type and from 80% to 50% and more particularly from 75 to 60% are of the oil-in-water type.

Its oil phase represents from 15% to 40% and preferably from 20% to 25% of its total weight. This latex can additionally comprise one or more additives chosen in particular from complexing agents, transfer agents or chain-limiting agents.

A subject-matter of the invention is also a cosmetic, dermocosmetic, dermopharmaceutical or pharmaceutical composition, characterized in that it comprises as thickening compound, at least one inverse latex as defined above.

The cosmetic, dermocosmetic, dermopharmaceutical or pharmaceutical composition defined above generally comprises from 0.1% to 10% and more particularly between 0.5% and 5% by weight of the said inverse latex. It is provided in particular in the form of a milk, of a lotion, of a gel, of a cream, of a soap, of a foam bath, of a balm, of a shampoo or of a conditioner.

Generally, the said inverse latex can advantageously replace the products sold under the name Sepigel™ 305 or Sepigel™ 501 by the Applicant Company in cosmetic, dermopharmaceutical or pharmaceutical compositions as it also exhibits good compatibility with the other excipients used in the preparation of formations such as milks, lotions, creams, soaps, foam baths, balms, shampoos or conditioners. It can also be used in combination with the said Sepigel products. It is in particular compatible with the concentrates disclosed and claimed in international publications WO 92/06778, WO 95/04592, WO 95/13863, WO 98/47610 or FR 2734 496 or with the surface-active agents disclosed in WO 93/08204.

It is particularly compatible with Montanov™ 68, Montanov™ 82, Montanov™ 202, Montanov™ WO18, Montanov™ S or Sepiperl™ N. It can also be used in emulsions of the type of those disclosed in EP 0 629 396 and in cosmetically or physiologically acceptable aqueous dispersions with an organopolysiloxane compound chosen, for example, from those disclosed in WO 93/05762 or in WO 93/21316. It can also be used to form cosmetically or physiologically acceptable aqueous gels with an acidic pH, such as those disclosed in WO 93/97856; it can also be used in combination with nonionic celluloses to form, for example, styling gels, such as those disclosed in EP 0 684 024, or in combination with esters of fatty acids and of sugar to form compositions for the treatment of the hair or of the skin, such as those disclosed in EP 0 603 019, or in shampoos or conditioners, such as disclosed and claimed in WO 92/21316, or finally in combination with an anionic homopolymer, such as Carbopol™, to form hair treatment products, such as those disclosed in DE 195 23596. It is also compatible with numerous active principles, such as, for example, self-tanning agents, such as dihydroxyacetone (DHA), or antiacne agents; it can thus be introduced into self-tanning compositions, such as those claimed in EP 0 715 845, EP 0 604 249 or EP 0 576 188 or in WO 93/07902. It is also compatible with N-acylated derivatives of amino acids, which allows it to be used in soothing compositions, in particular for sensitive skin, such as those disclosed or claimed in WO 92/21318, WO 94/27561 or WO 98/09611. It is also compatible with glycolic acids, with lactic acid, with salicylic acid, retinoids, phenoxyethanol, sugars, glyceraldehyde, xanthans, fruit acids and the various polyols used in the manufacture of cosmetic formulations.

Another subject-matter of the invention is thus the use of an inverse latex as defined above in preparing a cosmetic, dermocosmetic, dermopharmaceutical or pharmaceutical composition.

The examples which follow have the aim of illustrating the present invention without, however, limiting it. They show that the novel inverse latices do not irritate the skin and that their physical properties allow them to be used in the preparation of cosmetic, dermopharmaceutical or pharmaceutical compositions intended more particularly for the treatment of sensitive skin.

A) Examples of preparations of compositions according to the invention

EXAMPLE 1

Inverse Latex of an AMPS/acrylamide Copolymer Crosslinked with Methylenebis(acrylamide) in Squalane (Composition 1)

a)—The following are charged to a beaker with stirring:

288.0 g of a commercial 50% acrylamide solution, 363.0 g of a commercial 55% sodium 2-methyl-2-[(1-oxo-2-propenyl)amino]-1-propanesulphonate solution, 0.45 g of a commercial 40% by weight aqueous sodium diethylenetriaminepentaacetate solution, and 0.09 g of methylenebis(acrylamide).

The pH of this aqueous solution is adjusted to 5.0 by addition of approximately 0.4 g of 2-methyl-2-[(1-oxo-2-propenyl)amino]-1-propanesulphonic acid.

b)—An organic phase is prepared by mixing:

247.7 g of squalane, 19.5 g of Montane™ 80 VG, 11.5 g of Montanox™ 81 VG, and 0.27 g of azobis(isobutyronitrile).

c)—The aqueous phase is gradually introduced into the organic phase and the combined mixture is vigorously stirred by means of an Ultra-Turrax™ stirrer sold by IKA. The emulsion obtained is then transferred into a polymerization reactor, subjected to nitrogen sparging and then cooled to approximately 5–6° C. 10 ml of a solution comprising 0.28% by weight of cumene hydroperoxide in squalane are then added and then, after homogenizing the solution, an aqueous sodium metabisulphite solution (2.5 g in 100 ml of water) is added at the rate of 0.5 ml/minute over approximately 60 minutes while allowing the temperature to rise to the polymerization temperature. The reaction medium is then maintained for approximately 90 minutes at this temperature, on conclusion of which the mixture obtained is cooled to approximately 35°. 48.1 g of ethoxylated sorbitan oleate comprising 20 mol (Montanox™ 80) are slowly introduced and the desired water-in-oil emulsion is obtained.

Physical Properties

Viscosity in water at 3% of the latex (Brookfield RVT, Rotor 6, speed 5): η=100 000 mPa.s Viscosity in water at 3% of the latex (Brookfield RVT, Rotor 6, speed 20): η=33 800 mPa.s.

EXAMPLE 2

Inverse Latex of an AMPS/acrylamide Copolymer Crosslinked with Methylenebis(acrylamide) in Hydrogenated Polyisobutene (Composition 2)

a)—The following are charged to a beaker with stirring:

288.0 g of a commercial 50% acrylamide solution, 363.0 g of a commercial 55% sodium 2-methyl-2-[(1-oxo-2-propenyl)amino]-1-propanesulphonate solution, 0.45 g of a commercial 40% by weight aqueous sodium diethylenetriaminepentaacetate solution, and 0.09 g of methylenebis(acrylamide).

The pH of this aqueous solution is adjusted to 5.0 by addition of approximately 0.4 g of 2-methyl-2-[(1-oxo-2-propenyl)amino]-1-propanesulphonic acid.

b)—An organic phase is prepared by mixing:

235.5 g of hydrogenated polyisobutene, 15.1 g of Montane™ 80 VG, 7.4 g of Montanox™ 81 VG, and 0.25 g of azobis(isobutyronitrile).

c)—The aqueous phase is gradually introduced into the organic phase and the combined mixture is vigorously stirred by means of an Ultra-Turrax™ stirrer sold by IKA. The emulsion obtained is then transferred into a polymerization reactor, subjected to nitrogen sparging and then cooled to approximately 5–6° C. 10 ml of a solution comprising 0.28% by weight of cumene hydroperoxide in hydrogenated polyisobutene are then added and then, after homogenizing the solution, an aqueous sodium metabisulphite solution (2.5 g in 100 ml of water) is added at the rate of 0.5 ml/minute over approximately 60 minutes while allowing the temperature to rise to the polymerization temperature. The reaction medium is then maintained for approximately 90 minutes at this temperature, on conclusion of which the mixture obtained is cooled to approximately 35°. 25 g of ethoxylated sorbitan oleate comprising 20 mol (Montanox™ 80) are slowly introduced and the desired water-in-oil emulsion is obtained.

Physical Properties

Viscosity in water at 3% of the latex (Brookfield RVT, Rotor 6, speed 5): $\eta$=120 000 mPa.s Viscosity in water at 3% of the latex (Brookfield RVT, Rotor 6, speed 20): $\eta$=37 000 mPa.s.

EXAMPLE 3

Inverse Latex of an AMPS/acrylamide Copolymer Crosslinked with Methylenebis(acrylamide) in Marcol™52 (Composition 3)

a)—The following are charged to a beaker with stirring:
293.8 g of a commercial 50% acrylamide solution,
369.2 g of a commercial 55% sodium 2-methyl-2-[(1-oxo-2-propenyl)amino]-1-propanesulphonate solution,
0.45 g of a commercial 40% by weight aqueous sodium diethylenetriaminepentaacetate solution, and
0.131 g of methylenebis(acrylamide).

The pH of this aqueous solution is adjusted to 5.0 by addition of approximately 0.4 g of 2-methyl-2-[(1-oxo-2-propenyl)amino]-1-propanesulphonic acid.

b)—An organic phase is prepared by mixing:
235.5 g of Marcol™52,
15.1 g of Montane™ 80 VG,
7.1 g of Montanox™ 81 VG, and
0.25 g of azobis(isobutyronitrile).

c)—The aqueous phase is gradually introduced into the organic phase and the combined mixture is vigorously stirred by means of an Ultra-Turrax™ stirrer sold by IKA. The emulsion obtained is then transferred into a polymerization reactor, subjected to nitrogen sparging and then cooled to approximately 5–6° C. 10 ml of a solution comprising 0.28% by weight of cumene hydroperoxide in Marcol™52 are then added and then, after homogenizing the solution, an aqueous sodium metabisulphite solution (2.5 g in 100 ml of water) is added at the rate of 0.5 ml/minute over approximately 60 minutes while allowing the temperature to rise to the polymerization temperature. The reaction medium is then maintained for approximately 90 minutes at this temperature, on conclusion of which the mixture obtained is cooled to approximately 35°. 24.4 g of ethoxylated sorbitan oleate comprising 20 mol (Montanox™ 80) are slowly introduced and the desired water-in-oil emulsion is obtained.

Physical Properties

Viscosity in water at 3% of the latex (Brookfield RVT, Rotor 6, speed 5): $\eta$=140 000 mPa.s Viscosity in water at 3% of the latex (Brookfield RVT, Rotor 6, speed 20): $\eta$=37 000 mPa.s.

EXAMPLE 4

Inverse Latex of an AMPS/acrylamide Copolymer Crosslinked with Triallylamine in Marcol™52 (Composition 4)

The preparation is carried out as in Example 3 but replacing the 0.131 g of methylenebis(acrylamide) with 1.01 g of triallylamine and the desired water-in-oil emulsion is obtained.

Evaluation of the Properties

Viscosity in water at 3% of the latex (Brookfield RVT, Rotor 6, speed 5), $\eta$=170 000 mPa.s Viscosity in water at 3% of the latex (Brookfield RTV, Rotor 6, speed 20), $\eta$=45 000 mPa.s.

EXAMPLE 5

Inverse Latex of an AMPS Homopolymer Crosslinked with Triallylamine in Squalane (Composition 5)

a)—The following are charged to a beaker with stirring:
660 g of a commercial 55% sodium 2-methyl-2-[(1-oxo-2-propenyl)amino]-1-propanesulphonate solution,
0.45 g of a commercial 40% by weight aqueous sodium diethylenetriaminepentaacetate solution, and
0.5 g of triallylamine.

The pH of this aqueous solution is adjusted to 5.0 by addition of approximately 0.4 g of 2-methyl-2-[(1-oxo-2-propenyl)amino]-1-propanesulphonic acid.

b)—An organic phase is prepared by mixing:
247.7 g of squalane,
19.5 g of Montane™ 80 VG,
11.5 g of Montanox™ 81 VG, and
0.27 g of azobis(isobutyronitrile).

c)—The aqueous phase is gradually introduced into the organic phase and the combined mixture is vigorously stirred by means of an Ultra-Turrax™ stirrer sold by IKA. The emulsion obtained is then transferred into a polymerization reactor, subjected to nitrogen sparging and then cooled to approximately 5–6° C. 10 ml of a solution comprising 0.28% by weight of cumene hydroperoxide in squalane are then added and then, after homogenizing the solution, an aqueous sodium metabisulphite solution (2.5 g in 100 ml of water) is added at the rate of 0.5 ml/minute over approximately 60 minutes while allowing the temperature to rise to the polymerization temperature. The reaction medium is then maintained for approximately 90 minutes at this temperature, on conclusion of which the mixture obtained is cooled to approximately 35°. 48.1 g of ethoxylated sorbitan oleate comprising 20 mol (Montanox™ 80) are slowly introduced and the desired water-in-oil emulsion is obtained.

Physical Properties

Viscosity in water at 3% of the latex (Brookfield RVT, Rotor 6, speed 5): $\eta$=70 000 mPa.s Viscosity in water at 3% of the latex (Brookfield RVT, Rotor 6, speed 20): $\eta$=20 000 mPa.s.

EXAMPLE 6

Inverse Latex of an AMPS/acrylamide Copolymer Crosslinked with Triallylamine in Squalane (Composition 6)

The preparation is carried out as in Example 1 but replacing the 0.09 g of methylenebis(acrylamide) with 1.01 g of triallylamine and the 48.1 g of Montanox™ 80 with 40 g of Simulsol™ SL8 and the desired water-in-oil emulsion is obtained.

Physical Properties

Viscosity in water at 3% of the latex (Brookfield RVT, Rotor 6, speed 5): $\eta$=105 000 mPa.s Viscosity in water at 3% of the latex (Brookfield RVT, Rotor 6, speed 20): η=34 000 mPa.s.

EXAMPLE 7

Inverse Latex of an AMPS/acrylamide Copolymer Crosslinked with Triallylamine in Isohexadecane (Composition 7)

a)—The following are charged to a beaker with stirring:
80 g of deionized water,
95.96 g of a 48% by weight sodium hydroxide solution,
253.8 g of a commercial 50% acrylamide solution,
246.7 g of 2-methyl-2-[(1-oxo-2-propenyl)amino]-1-propanesulphonic acid,
0.45 g of a commercial 40% by weight aqueous sodium diethylenetriaminepentaacetate solution, and
1.01 g of triallylamine.

The pH of this aqueous solution is adjusted to 5.0 and the aqueous phase is made up to 682 g by addition of deionized water.

b) n organic phase is prepared by mixing:
220 g of isohexadecane,
21 g of Montane™ 80 VG, and
0.2 g of azobis(isobutyronitrile).

c)—The aqueous phase is gradually introduced into the organic phase and the combined mixture is vigorously stirred by means of an Ultra-Turrax™ stirrer sold by IKA. The emulsion obtained is then transferred into a polymerization reactor, subjected to nitrogen sparging and then cooled to approximately 5–6° C. 5 ml of a solution comprising 0.28% by weight of cumene hydroperoxide in isohexadecane are then added and then, after homogenizing the solution, an aqueous sodium metabisulphite solution (2.5 g in 100 ml of water) is added at the rate of 0.5 ml/minute over approximately 60 minutes while allowing the temperature to rise to the polymerization temperature. The reaction medium is then maintained for approximately 90 minutes at this temperature, on conclusion of which the mixture obtained is cooled to approximately 35°. 50 g of ethoxylated sorbitan oleate comprising 20 mol (Montanox™ 80) are slowly introduced and the desired water-in-oil emulsion is obtained.

Physical Properties

Viscosity in water a 2% of the latex (Brookfield RVT, Rotor 6, speed 5): η=69 000 mPa.s
Viscosity in water at 2% of the latex (Brookfield RVT, Rotor 6, speed 20): η=23 450 mPa.s.

B) Properties of the compositions according to the invention
a)—Temperature stability A cream gel comprising 3% of Composition 4 and 20% of cetearyl octanoate was prepared and the viscosity was measured.

The results are recorded in the following table:

|  | Viscosity, Brookfield LVT, 6 rpm (in mPa.s) | |
| --- | --- | --- |
|  | At ambient temperature | At 50° C. |
| After 1 day | 100 000 | 100 000 |
| After 7 days | 100 000 | 100 000 |
| After 1 month | 100 000 | 100 000 | b)—Stability towards UV radiation

It is found that the gel prepared with Composition 4 is very stable towards UV radiation as its viscosity did not vary after exposure for 14 days.

c)—Influence of the pH on the viscosity

The viscosity of the cream gel prepared with Composition 4 is very stable to pH in the range pH=3 to pH=8.

d) Comparative study of cutaneous tolerance

The local epicutaneous tolerance of a series of cream gels, comprising 3% and 5% by weight of one of Compositions 1 to 7 prepared as described above, was determined and compared with that observed with an inverse latex of an AMPS/acrylamide copolymer crosslinked with methylenebis(acrylamide) in Isopar™ M (Composition A), according to the following protocol:

The test composition is applied to an area of approximately 50 mm$^2$ of the left subscapular region of the skin (of "Japanese skin" type) of the backs of 19 healthy volunteers. Contact is maintained for 48 hours under an occlusive patch.

This application is also carried out under the same conditions with a patch alone (without composition) as negative control.

Clinical observation of the skin area thus treated is carried out 30 minutes and then 24 hours after removing the said patches. These observations are made by comparison with the untreated negative control area.

Quantification of the cutaneous irritation, according to a numerical scale ranging from 0 to 4 (0: no effect; 1: very slight effect; 2: distinct effect; 3 and 4: moderate to severe effect depending on the reactions), is carried out for each of the reactions observed, namely: erythema, oedema, blisters, dryness of the skin, roughness of the skin and reflectivity of the skin.

The cutaneous tolerance indices (CI) given in the following table express the mean of the sum of the quantified effects recorded for each volunteer:

CI=0 means that no irritation was observed,
CI=0.5 means that the product is statistically well tolerated,
CI>0.5 means that the product results in intolerance.

|  | Cutaneous tolerance index | |
| --- | --- | --- |
|  | 3% gel | 5% gel |
| Composition 1 | 0.11 | 0.21 |
| Composition 2 | 0.89 | 0.63 |
| Composition 3 | 0.26 | 0.26 |
| Composition 4 | 0.26 | 0.26 |
| Composition 7 | 0.32 | 1.0 |
| Composition A | 2.42 | 3.20 |

These results show that, unexpectedly, squalane, hydrogenated polyisobutene, isohexadecane and Marcol™52 potentiate cutaneous tolerance of the inverse latex.

C) Examples of formulations prepared with the compositions according to the invention Example 8: Care cream

| Cyclomethicone: | 10% |
| --- | --- |
| Composition 4: | 0.8% |
| Montanov ™ 68: | 2% |
| Stearyl alcohol: | 1% |

| | | |
|---|---|---|
| Stearic alcohol: | | 0.5% |
| Preservative: | | 0.65% |
| Lysine: | | 0.025% |
| EDTA (disodium salt): | | 0.05% |
| Xanthan gum: | | 0.2% |
| Glycerol: | | 3% |
| Water: | | q.s. for 100% |

Example 9: Aftershave balm

FORMULA

| | | |
|---|---|---|
| A | Composition 4: | 1.5% |
| | Water: | q.s. for 100% |
| B | micropearl ™ M 100: | 5.0% |
| | Sepicide ™ CI: | 0.50% |
| | Fragrance: | 0.20% |
| | 95° Ethanol: | 10.0% |

PROCEDURE
  B is added to A.

Example 10: Satin emulsion for the body

FORMULA

| | | |
|---|---|---|
| A | Simulsol ™ 165: | 5.0% |
| | Lanol ™ 1688: | 8.50% |
| | Karite butter: | 2% |
| | Liquid paraffin: | 6.5% |
| | Lanol ™ 14M: | 3% |
| | Lanol ™ S: | 0.6% |
| B | Water: | 66.2% |
| C | Micropearl ™ M 100: | 5% |
| D | Composition 3: | 3% |
| E | Sepicide ™ CI: | 0.3% |
| | Sepicide ™ HB: | 0.5% |
| | Monteine ™ CA: | 1% |
| | Fragrance: | 0.20% |
| | Vitamin E acetate: | 0.20% |
| | Sodium pyrrolidinonecarboxylate: | 1% |

PROCEDURE
  C is added to B, B is emulsified in A at 70° C.,
  D is then added at 60° C. and then E is added at 30° C.

Example 11: O/W cream

FORMULA

| | | |
|---|---|---|
| A | Simulsol ™ 165: | 5.0% |
| | Lanol ™ 1688: | 20.0% |
| | Lanol ™ P: | 1.0% |
| B | Water: | q.s. for 100% |
| C | Composition 3: | 2.50% |
| E | Sepicide ™ CI: | 0.20% |
| | Sepicide ™ HB: | 0.30% |

PROCEDURE
  B is introduced into A at approximately 75° C., C
  is added at approximately 60° C. and then D is added at
  approximately 45° C.

Example 12: Non-greasy antisun gel

FORMULA

| | | |
|---|---|---|
| A | Composition 5: | 3.00% |
| | Water: | 30% |
| B | Sepicide ™ CI: | 0.20% |
| | Sepicide ™ HB: | 0.30% |
| | Fragrance: | 0.10% |
| C | Colorant: | q.s. |
| | Water: | 30% |
| D | Micropearl ™ M 100: | 3.00% |
| | Water: | q.s. for 100% |
| E | Silicone oil: | 2.0% |
| | Parsol ™ MCX: | 5.00% |

PROCEDURE
  B is introduced into A, C is added, then D is
  added and then E is added.

Example 13: Antisun milk

FORMULA

| | | |
|---|---|---|
| A | Montanov ™ S: | 3.0% |
| | Sesame oil: | 5.0% |
| | Parsol ™ MCX: | 5.0% |
| | λ-Carrageenan: | 0.10% |
| B | Water: | q.s. for 100% |
| C | Composition 1: | 0.80% |
| D | Fragrance: | q.s. |
| | Preservative: | q.s. |

PROCEDURE
  B is emulsified in A at 75° C., then C is added
  at approximately 60° C., then D is added at approximately
  30° C. and the pH is adjusted, if necessary.

Example 14: Massage gel

FORMULA

| | | |
|---|---|---|
| A | Composition 2: | 3.5% |
| | Water: | 20.0% |
| B | Colorant: | 2 drops/100 g |
| | Water: | q.s. |
| C | Alcohol: | 10% |
| | Menthol: | 0.10% |
| D | Silicone oil: | 5.0% |

PROCEDURE
  B is added to A, then C is added to the mixture
  and then D is added to the mixture.

Example 15: Moisturizing and mattifying foundation

FORMULA

| | | |
|---|---|---|
| A | Water: | 20.0% |
| | Butylene glycol | 4.0% |
| | PEG-400: | 4.0% |
| | Pecosil ™ PS100: | 1.0% |
| | NaOH: | q.s. pH = 9 |
| | Titanium dioxide: | 7.0% |
| | Talc: | 2.0% |
| | Yellow iron oxide: | 0.8% |
| | Red iron oxide: | 0.3% |
| | Black iron oxide: | 0.05% |
| B | Lanol ™ 99: | 8% |
| | Caprylic/capric triglyceride | 8% |
| | Montanov ™ 202: | 5.00% |
| C | Water: | q.s. for 100% |
| | Micropearl ™ M305: | 2.0% |
| | Tetrasodium EDTA: | 0.05% |
| D | Cyclomethicone: | 4.0% |
| | Xanthan gum: | 0.2% |
| | Composition 4: | 0.8% |
| E | Sepicide ™ HB: | 0.5% |
| | Sepicide ™ CI: | 0.3% |
| | Fragrance: | 0.2% |

PROCEDURE
  The B + D and A + C mixtures are prepared at
  80° C. and then all the ingredients are mixed and
  emulsified.

Example 16: Radiance gel

FORMULA

| | | |
|---|---|---|
| A | Composition 6: | 4% |
| | Water: | 30% |
| B | Elastine HPM: | 5.0% |
| C | Micropearl ™ M 100: | 3% |
| | Water: | |
| D | Sepicide ™ CI: | 0.2% |
| | Sepicide ™ HB: | 0.3% |
| | Fragrance: | 0.06% |
| | 50% sodium pyrrolidinonecarboxylate: | 1% |
| | Water: | q.s. for 100% |

PROCEDURE
  A is prepared, B is added, then C is added and
  then D is added.

Example 17: Body milk

FORMULA

| | | |
|---|---|---|
| | Montanov ™ S: | 3.5% |
| | Lanol ™ 37T: | 8.0% |
| | Solagum ™ L: | 0.05% |
| | Water: | q.s. for 100% |
| | Benzophenone: | 2.0% |
| | Dimethicone 350 cPs: | 0.05% |
| | Composition 5: | 0.8% |
| | Preservative: | 0.2% |
| | Fragrance: | 0.4% |

Example 18: Make-up-removing emulsion comprising sweet almond oil

FORMULA
| | |
|---|---|
| Montanov ™ 68: | 5% |
| Sweet almond oil: | 5% |
| Water: | q.s. for 100% |
| Composition 4: | 0.3% |
| Glycerol: | 5% |
| Preservative: | 0.2% |
| Fragrance: | 0.3% |

Example 19: Moisturizing cream for greasy skin

FORMULA
| | |
|---|---|
| Montanov ™ 68: | 5% |
| Cetylstearyl octanoate: | 8% |
| Octyl palmitate: | 2% |
| Water: | q.s. for 100% |
| Composition 3: | 0.6% |
| Micropearl ™ M100: | 3.0% |
| Mucopolysaccharides: | 5% |
| Sepicide ™ HB: | 0.8% |
| Fragrance: | 0.3% |

Example 20: Alcohol-free soothing aftershave balm

FORMULA
| | | |
|---|---|---|
| A | Lipacide ™ PVB: | 1.0% |
| | Lanol ™ 99: | 2.0% |
| | Sweet almond oil: | 0.5% |
| B | Composition 4: | 3.5% |
| C | Water: | q.s. for 100% |
| D | Fragrance: | 0.4% |
| | Sepicide ™ HB: | 0.4% |
| | Sepicide ™ CI: | 0.2% |

Example 21: Cream with AHAs for sensitive skin

FORMULA
| | |
|---|---|
| Mixture of lauryl amino acids: | 0.1% to 5% |
| Magnesium potassium aspartate: | 0.002% to 0.5% |
| Lanol ™ 99: | 2% |
| Montanov ™ 68: | 5.0% |
| Water: | q.s. for 100% |
| Composition 2: | 1.50% |
| Gluconic acid: | 1.50% |
| Triethylamine: | 0.9% |
| Sepicide ™ HE: | 0.3% |
| Sepicide ™ CI: | 0.2% |
| Fragrance: | 0.4% |

Example 22: Aftersun soothing care preparation

FORMULA
| | |
|---|---|
| Mixture of lauryl amino acids: | 0.1% to 5% |
| Magnesium potassium aspartate: | 0.002% to 0.5% |
| Lanol ™ 99: | 10.0% |
| Water: | q.s. for 100% |
| Composition 4: | 2.50% |
| Sepicide ™ HB: | 0.3% |
| Sepicide ™ CI: | 0.2% |
| Fragrance: | 0.4% |
| Colorant: | 0.03% |

Example 23: Make-up-removing milk

FORMULA
| | |
|---|---|
| Sepiperl ™ N: | 3% |
| Primol ™ 352: | 8.0% |
| Sweet almond oil: | 2% |
| Water: | q.s. for 100% |
| Composition 2: | 0.8% |
| Preservative: | 0.2% |

Example 24: Fluid emulsion with an alkaline pH

| | |
|---|---|
| Marcol ™ 82: | 5.0% |
| NaOH: | 10.0% |
| Water: | q.s. for 100% |
| Composition 1: | 1.5% |

Example 25: Liquid foundation

FORMULA
| | |
|---|---|
| Simulsol ™ 165: | 5.0% |
| Lanol ™ 84D: | 8.0% |
| Lanol ™ 99: | 5.0% |
| Water: | q.s. for 100% |
| Inorganic pigments and fillers: | 10.0% |
| Composition 1: | 1.2% |
| Preservative: | 0.2% |
| Fragrance: | 0.4% |

Example 26: Antisun milk

FORMULA
| | |
|---|---|
| Sepiperl ™ N: | 3.5% |
| Lanol ™ 37T: | 10.0% |
| Parsol ™ MCX: | 5.0% |
| Eusolex ™ 4360: | 2.0% |
| Water: | q.s. for 100% |
| Composition 4: | 1.8% |
| Preservative: | 0.2% |
| Fragrance: | 0.4% |

Example 27: Eye contour gel

FORMULA
| | |
|---|---|
| Composition 1: | 2.0% |
| Fragrance: | 0.06% |
| Sodium pyrrolidinonecarboxylate: | 0.2% |
| Dow Corning ™ 245 Fluid: | 2.0% |
| Water: | q.s. for 100% |

Example 28: Leave-on care composition

FORMULA
| | |
|---|---|
| Composition 6: | 1.5% |
| Fragrance: | q.s. |
| Preservative: | q.s. |
| Dow Corning ™ X2 8360: | 5.0% |
| Dow Corning ™ Q2 1401: | 15.0% |
| Water: | q.s. for 100% |

Example 29: Slimming gel

| | |
|---|---|
| Composition 6: | 5% |
| Ethanol: | 30% |
| Menthol: | 0.1% |
| Caffeine: | 2.5% |
| Ruscus extract: | 2% |
| Ivy extract: | 2% |
| Sepicide ™ HP: | 1% |
| Water: | q.s. for 100% |

Example 30: Ultranatural tinted cream gel

FORMULA
| | | |
|---|---|---|
| A | Water: | 10.0% |
| | Butylene glycol: | 4.0% |
| | PEG-400: | 4.0% |
| | Pecosil ™ PS100: | 1.5% |
| | NaOH: | q.s. pH = 7 |
| | Titanium dioxide: | 2.0% |
| | Yellow iron oxide: | 0.8% |
| | Red iron oxide: | 0.3% |
| | Black iron oxide: | 0.05% |
| B | Lanol ™ 99: | 4.0% |
| | Caprylic/capric triglyceride: | 4.0% |
| | Sepifeel ™ ONE: | 1.0% |
| | Composition 2: | 3.0% |
| C | Water: | q.s. for 100% |
| | Micropearl ™ M305: | 2.0% |
| | Tetrasodium EDTA: | 0.05% |
| | Cyclomethicone: | 4.0% |
| D | Sepicide ™ HB: | 0.5% |
| | Sepicide ™ CI: | 0.3% |
| | Fragrance: | 0.2% |

PROCEDURE
The B + C mixture is prepared, then A is added and then D is added.

Example 31: Care preparation for greasy skin

FORMULA
| | | |
|---|---|---|
| A | Micropearl ™ M310: | 1.0% |
| | Composition 4: | 5.0% |
| | Octyl isononanoate: | 4.0% |
| B | Water: | q.s. for 100% |

Example 32: Cream comprising AHAs

FORMULA

| | | |
|---|---|---|
| A | Montanov ™ 68: | 5.0% |
| | Lipacide ™ PVB: | 1.05% |
| | Lanol ™ 99: | 10.0% |
| B | Water: | q.s. for 100% |
| | Gluconic acid | 1.5% |
| | TEA (triethanolamine): | 0.9% |
| C | Composition 2: | 1.5% |
| D | Fragrance: | 0.4% |
| | Sepicide ™ HB: | 0.2% |
| | Sepicide ™ CI: | 0.4% |

Example 33: Non-greasy self-tanning preparation for the face and body

FORMULA

| | | |
|---|---|---|
| A | Lanol ™ 2681: | 3.0% |
| | Composition 4: | 2.5% |
| B | Water: | q.s. for 100% |
| | Dihydroxyacetone: | 3.0% |
| C | Fragrance: | 0.2% |
| | Sepicide ™ HB: | 0.8% |
| | NaOH (sodium hydroxide): | q.s. pH = 5 |

Example 34: Anti-sun milk comprising Tahitian perfumed oil

FORMULA

| | | |
|---|---|---|
| A | Tahitian perfumed oil | 10% |
| | Lipacide ™ PVB: | 0.5% |
| | Composition 5: | 2.2% |
| B | Water: | q.s. for 100% |
| C | Fragrance: | 0.1% |
| | Sepicide ™ HB: | 0.3% |
| | Sepicide ™ CI: | 0.1% |
| | Parsol ™ MCX: | 4.0% |

Example 35: Antisun care preparation for the face

FORMULA

| | | |
|---|---|---|
| A | Cyclomethicone and dimethiconol: | 4.0% |
| | Composition 2: | 3.5% |
| B | Water: | q.s. for 100% |
| C | Fragrance: | 0.1% |
| | Sepicide ™ HB: | 0.3% |
| | Sepicide ™ CI | 0.21% |
| | Parsol ™ MCX: | 5.0% |
| | Titanium oxide-Coated mica | 2.0% |
| | Lactic acid: | q.s. pH = 6.5 |

Example 36: Sunless tanning emulsion

FORMULA

| | | |
|---|---|---|
| A | Lanol ™ 99: | 15% |
| | Montanov ™ 68: | 5.0% |
| | Parsol ™ MCX: | 3.0% |
| B | Water: | q.s. for 100% |
| | Dihydroxyacetone: | 5.0% |
| | Monosodium phosphate: | 0.2% |
| C | Composition 4: | 0.5% |
| D | Fragrance: | 0.3% |
| | Sepicide ™ HB: | 0.8% |
| | NaOH: | q.s. pH = 5 |

The characteristics of the products used in the preceding examples are as follows:

Montanov™ 68 (cetearyl glucoside, cetearyl alcohol) is a self-emulsifiable composition, such as those disclosed in WO 92/06778, sold by Seppic.

Montanov™ 202 (arachidyl glucoside, arachidyl alcohol+ behenyl alcohol) is a self-emulsifiable composition, such as those disclosed in WO 98/17610, sold by Seppic.

Micropearl™ M 305 is a silky water-dispersible powder based on crosslinked methyl methacrylate copolymer.

Micropearl™ M 100 is an ultrafine powder with a very soft feel and with a mattifying action, sold by Matsumo.

Sepicide™ CI, imidazolineurea, is a preservative sold by Seppic.

Pemulen™ TR is an acrylic polymer sold by Goodrich.

Simulsol™ 165 is self-emulsifiable glycerol stearate, sold by Seppic.

Lanol™ 1688 is an emollient ester with a non-greasy effect sold by Seppic.

Lanol™ 14M and Lanol™ S are consistency factors sold by Seppic.

Sepicide™ HB, which is a mixture of phenoxyethanol, methylparaben, ethylparaben, propylparaben and butylparaben, is a preservative sold by Seppic.

Monteire™ CA is a moisturizing agent sold by Seppic.

Schercemol™ OP is an emollient ester with a non-greasy effect.

Lanol™ P is an additive with a stabilizing effect sold by Seppic.

Sepiperim™ N is a pearlescent agent, sold by Seppic, based on a mixture of alkyl polyglucosides such as those disclosed in WO 95/13863.

Montanov™ S is a pearlescent agent, sold by Seppic, based on a mixture of alkyl polyglucosides such as those disclosed in WO 95/13863.

Pecosil™ PS 100 is dimethicone copolyol phosphate, sold by Phoenix.

Lanol™ 99 is isononyl isononanoate, sold by Seppic.

Lanol™ 37T is glycerol triheptanoate, sold by Seppic.

Sepifeel™ ONE is a mixture of palmitoylproline, magnesium palmitoylglutamate and magnesium palmitoylsarcosinate, such as those disclosed in FR 2 787 323.

Solagum™ L is a carrageenan sold by Seppic.

Marcol™ 82 is a liquid paraffin sold by Esso.

Lanol™ 84D is dioctyl malate, sold by Seppic.

Parsol™ MCX is ethylhexyl para-methoxycinnamate, sold by Givaudan.

Eusolex™ 4360 is benzophenone-3, sold by Merck.

Dow Corning™ 245 Fluid is cyclomethicone, sold by Dow Corning.

Lipacide™ PVB is a hydrolysate of palmitoylated wheat proteins sold by Seppic.

Sepicontrol™ A5 is a capryloylglycine, sarcosine, extract of Cinnamon zylanicum mixture sold by Seppic, such as those disclosed in International Patent Application PCT/FR98/01313 filed on Jun. 23, 1998.

Capigel™ 98 is an acrylates copolymer sold by Seppic.

Lanol™ 2681 is a coconut caprylate/caprate mixture sold by Seppic.

What is claimed is:

1. A composition, comprising:
an oil phase, an aqueous phase, at least one emulsifying agent of water-in-oil (W/O) type and at least one emulsifying agent of oil-in-water (O/W) type in the form of a self-invertible inverse latex comprising from 20% to 70% by weight of a branched or crosslinked polyelectrolyte, wherein
a constituent solvent of the oil phase is selected from the group consisting of squalane and hydrogenated polyisobutene, and the polyelectrolyte is selected from the group, consisting of a homopolymer based on a monomer having a partially or completely salified strong acid functional group and a copolymer based on at least one monomer having a partially or completely salified strong acid functional group copolymerized with acrylamide with a crosslinking and/or branching agent of diallyloxyacetic acid or one of its salts; or the constituent solvent of the oil phase is selected from the group consisting of white mineral oils, isohexadecane, and isododecane, and the polyelectrolyte is a copolymer based on at least one monomer having a partially or completely salified strong acid functional group copolymerized with acrylamide with the crosslinking and/or branching agent being triallylamine.

2. The composition as defined in claim 1, in which the constituent solvent of the oil phase is a white mineral oil.

3. The composition as defined in claim 1, wherein the constituent solvent of the oil phase is hydrogenated polyisobutene.

4. The composition as defined in claim 1, wherein the constituent solvent of the oil phase is squalane.

5. The composition as defined in claim 1, wherein the constituent solvent of the oil phase is isohexadecane.

6. The composition as defined in claim 1, wherein the constituent solvent of the oil phase is isododecane.

7. The composition as defined in claim 1, wherein the emulsifying agent or agents of the water-in-oil type are chosen from sorbitan monooleate, sorbitan isostearate or sorbitan oleate ethoxylated with 5 mol of ethylene oxide.

8. The composition as defined in claim 1, in which the emulsifying agent or agents of the oil-in-water type are chosen from sorbitan oleate ethoxylated with 20 mol of ethylene oxide, ethoxylated castor oil comprising 40 mol of ethylene oxide, ethoxylated sorbitan laurate comprising 20 mol of ethylene oxide or ethoxylated lauryl alcohol comprising 7 mol of ethylene oxide.

9. The composition as defined in claim 1, in which the emulsifying agent or agents of the oil-in-water type are chosen from compounds having formula (I):

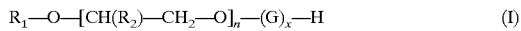

$$R_1-O-[CH(R_2)-CH_2-O]_n-(G)_x-H \qquad (I)$$

wherein $R_1$ represents a hydrocarbonaceous radical comprising from 1 to 30 carbon atoms, $R_2$ represents a hydrogen atom or an alkyl radical comprising 1 or 2 carbon atoms, G represents the residue of a saccharide, x represents a decimal number between 1 and 5 and n is equal either to zero or to an integer between 1 and 30.

10. The composition as defined in claim 9 wherein, in the formula (I), the number x is between 1 and 3.

11. The composition as defined in claim 9 for which, in the formula (I), G represents the glucose residue or the xylose residue and n is equal to 0.

12. The composition as defined in claim 9 for which, in the formula (I), $R_1$ represents a radical having from 8 to 18 carbon atoms.

13. The composition as defined in claim 1 wherein the strong acid functional group of the monomer is a partially or completely salified sulphonic acid functional group or phosphonic acid functional group.

14. The composition as defined in claim 13 wherein said monomer comprising a strong acid functional group is 2-methyl-2-[(1-oxo-2-propenyl)amino]-1-propanesulphonic acid partially or completely salified in the form of sodium, potassium, ammonium or monoethanolamine salt.

15. The composition as defined in claim 1 wherein the polyelectrolyte is a copolymer comprising, in molar proportions, from 30% to 50% of 2-methyl-2-[(1-oxo-2-propenyl)amino]-1-propanesulphonic acid, salified in the form of the sodium salt or of the ammonium salt, and from 50% to 70% of acrylamide.

16. The composition as defined in claim 1 the polyelectrolyte is a homopolymer of 2-methyl-2-[(1-oxo-2-propenyl)amino]-1-propanesulphonic acid salified in the form of a sodium salt or an ammonium salt.

17. The composition as defined in claim 1, wherein the polyelectrolyte is crosslinked and/or branched with a diethylenic or polyethylenic compound in the molar proportion, expressed with respect to the monomers employed, of 0.005% to 1%.

18. The composition as defined in claim 1, further comprising from 4% to 10% by weight of emulsifying agents.

19. The composition as defined in claim 18, wherein from 20% to 50% of the total weight of the emulsifiers are of the water-in-oil type and from 80% to 50% are of the oil-in-water type.

20. The composition as defined in claim 1, wherein said oil phase represents from 15% to 40% of its total weight.

21. The composition as defined in claim 1, further comprising one or more additives chosen from complexing agents, transfer agents or chain-limiting agents.

22. A cosmetic, dermocosmetic, dermopharmaceutical or pharmaceutical composition, comprising from 0.1% to 10% by weight of the composition as defined in claim 1.

23. The cosmetic, dermocosmetic, dermopharmaceutical or pharmaceutical composition as defined in claim 22, wherein said composition is in the form of a milk, of a lotion, of a gel, of a cream, of a soap, of a foam bath, of a balm, of a shampoo or of a conditioner.

24. A cosmetic, dermocosmetic, dermopharmaceutical or pharmaceutical composition, comprising the composition according to claim 1.

* * * * *

UNITED STATES PATENT AND TRADEMARK OFFICE
CERTIFICATE OF CORRECTION

PATENT NO.    : 6,673,861 B2                                      Page 1 of 1
DATED         : January 6, 2004
INVENTOR(S)   : Guy Tabacchi et al.

It is certified that error appears in the above-identified patent and that said Letters Patent is hereby corrected as shown below:

<u>Title page,</u>
Item [75], should read as follows:
-- [75] Inventors: Guy Tabacchi, Castres (FR);
                Jean-Pierre Boiteux, Saix (FR);
                Chantal Amalric, Blan (FR); Nelly
                Michel, Maisons Alfort (FR); Paul
                Mallo, Chatou (FR) --

Signed and Sealed this

Thirteenth Day of April, 2004

JON W. DUDAS
*Acting Director of the United States Patent and Trademark Office*